(12) United States Patent
Vandenmersch et al.

(10) Patent No.: US 7,071,354 B2
(45) Date of Patent: Jul. 4, 2006

(54) METHOD FOR PRODUCING N-PHOSPHONOMETHYLGLYCINE

(75) Inventors: Hugues Vandenmersch, Wachenheim (DE); Hartwig Voss, Frankenthal (DE); Stefan Orsten, Ellerstadt (DE); Christian Wulff, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 12 days.

(21) Appl. No.: 10/481,565

(22) PCT Filed: Jun. 21, 2002

(86) PCT No.: PCT/EP02/06903

§ 371 (c)(1),
(2), (4) Date: Dec. 22, 2003

(87) PCT Pub. No.: WO03/000704

PCT Pub. Date: Jan. 3, 2003

(65) Prior Publication Data

US 2004/0235664 A1     Nov. 25, 2004

(30) Foreign Application Priority Data

Jun. 22, 2001   (DE) ................................ 101 30 136

(51) Int. Cl.
*C07F 9/22* (2006.01)
*C07F 9/28* (2006.01)

(52) U.S. Cl. .................................... 562/17; 504/206
(58) Field of Classification Search .................. 562/17; 504/206
See application file for complete search history.

(56) References Cited

U.S. PATENT DOCUMENTS 3,950,402 A    4/1976  Franz
3,969,398 A    7/1976  Hershman
4,486,359 A    12/1984 Brendel nee Hajnoczki et al.

FOREIGN PATENT DOCUMENTS

| DE | 25 28633     | 2/1976  |
| EP | 0 806 428 A1 * | 11/1997 |
| EP | 806 428      | 11/1997 |
| IT | 1 281 094    | 2/1998  |
| WO | 96 33005     | 10/1996 |
| WO | 01/47938     | 7/2001  |
| WO | 01/79214     | 10/2001 |

OTHER PUBLICATIONS

Jaron et al., Chem Abst. Am.Chem.Soc. vol. 11, No. 4 122, Mar. 1995, Preparation of N-Phosphomethylglycine.

* cited by examiner

*Primary Examiner*—Johann Richter
*Assistant Examiner*—Chukwuma Nwaonicha
(74) *Attorney, Agent, or Firm*—Novak Druce & Quigg; Jason D. Voight

(57) ABSTRACT

The present invention relates to a process for the recovery of N-phosphonomethylglycine from an aqueous mixture which contains N-phosphonomethylglycine, ammonium halides, and alkali metal or alkaline earth metal halides and optionally organic impurities in dissolved form, where (a) the pH of the mixture is adjusted to a value in the range from 2 to 8,
(b) a separation of the mixture on a selective nanofiltration membrane is performed, a retentate which is richer in N-phosphonomethylglycine and poorer in halides and a permeate which is richer in halides and poorer in N-phosphonomethylglycine being obtained, and
(c) the N-phosphonomethylglycine is recovered from the retentate.

The process according to the invention makes possible the recovery of the N-phosphonomethylglycine with simultaneous separation of the halide salts.

13 Claims, No Drawings

METHOD FOR PRODUCING N-PHOSPHONOMETHYLGLYCINE

The present invention relates to a process for the recovery of N-phosphonomethylglycine from a mixture which contains N-phosphonomethylglycine, chloride salts and optionally organic impurities.

N-Phosphonomethylglycine (glyphosate) is a total herbicide which is employed to a great extent. Numerous processes for the preparation of phosphonomethylglycine are known. In one of the most customary processes, the last stage consists in oxidizing phosphonomethyliminodiacetic acid or a salt thereof catalytically using air, oxygen or hydrogen peroxide. The oxidation is generally carried out in aqueous medium using carbon, molybdenum or vanadium salts, platinum, rhodium or palladium etc. as catalysts. In addition to N-phosphonomethylglycine, carbon dioxide and formaldehyde are formed here. A process of this type is described in U.S. Pat. No. 3,950,402 and U.S. Pat. No. 3,969,398.

Both the reaction mixture and the mother liquor which are obtained after recovery of the N-phosphonomethylglycine from the reaction mixture by crystallization thus contain formaldehyde, which is known to be carcinogenic. In IT 1281094 it is therefore proposed to remove the formaldehyde with the aid of a separation process using a selective membrane having a pore size in the range from 10 to 1000 nm. The formaldehyde is removed here via the permeate.

PCT/EP00/13162 describes a process for the preparation of N-phosphonomethylglycine, where a hexahydrotriazine derivative of the formula IIa

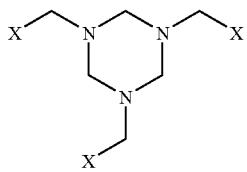

in which X, in particular, is CN, is reacted with a triacyl phosphite of the formula P(OCOR$^3$)$_3$, in which R$^3$, in particular, is phenyl, and the product obtained is hydrolyzed. The N-phosphonomethylglycine is recovered from the reaction mixture by crystallization at pH 0.5 to 2. The mother liquor has a completely different composition than the mother liquor obtained in the oxidation of phosphonomethyliminodiacetic acid. It additionally contains considerable amounts of N-phosphonomethylglycine, small amounts of aminomethylphosphonic acid, glycine and bis(phosphonomethyl)glycine, and large amounts of chloride salts. It would be desirable to minimize the losses of valuable substance and the pollution of the waste water.

The present invention is therefore based on the object of making available an economical process for the recovery of N-phosphonomethylglycine from an aqueous mixture which contains N-phosphonomethylglycine, ammonium salts, alkali metal or alkaline earth metal salts and optionally organic impurities in dissolved form. At the same time, the process should make possible a recovery of the N-phosphonomethylglycine which is as complete as possible and a recovery of the ammonia contained in the ammonium salts which is as complete as possible.

Surprisingly, it has now been found that this object is achieved if the aqueous mixture mentioned is subjected to a separation in a pressure-driven separation process using a selective nanofiltration membrane.

The present invention therefore relates to a process for the recovery of N-phosphonomethylglycine from an aqueous mixture which contains N-phosphonomethylglycine, ammonium halides, alkali metal or alkaline earth metal halides and optionally organic impurities in dissolved form, where
 a) the pH of the mixture is adjusted to a value in the range from 2 to 8,
 b) a separation of the mixture on a selective nanofiltration membrane is performed, a retentate which is enriched with N-phosphonomethylglycine and depleted in halides and a permeate which is enriched in the halides and depleted in N-phosphonomethylglycine being obtained, and
 c) N-phosphonomethylglycine is recovered, if desired, from the retentate.

N-Phosphonomethylglycine can be present in different ionic forms as a function of the pH. All these forms are included according to the invention.

The mixture used as a starting material is an aqueous mixture. It can optionally contain a small proportion, in particular up to 10% by weight, of a water-miscible solvent, for example a mono- or polyalcohol, such as methanol, ethanol, isopropanol, glycol, 1,2- or 1,3-propanediol etc, acetone, dioxane or tetrahydrofuran.

The mixture contains, based on the weight of N-phosphonomethylglycine, an excess of ammonium halides and alkali metal or alkaline earth metal halides. The ammonium halides, in addition to NH$_4$Hal, are also to be understood as meaning ammonium halides which are substituted by 1 to 3 C$_1$–C$_4$-alkyl or benzyl groups, e.g. methyl-, dimethyl-, trimethyl-, tributyl- and benzylammonium halide. Preferred alkali metal or alkaline earth metal halides are sodium, potassium and calcium halides. Chlorides are preferred as halides. The amount of halides is, in general, at least 8% by weight, in particular at least 10% by weight and particularly preferably at least 12% by weight, based on the total weight of the mixture. The amount of N-phosphonomethylglycine is in general less than 4% by weight and in particular less than 3% by weight. It is preferably in the range from 0.5 to 3.0% by weight.

According to a preferred embodiment, the mixture originates from the preparation of N-phosphonomethylglycine, in which a hexahydrotriazine derivative of the formula II

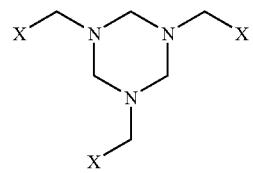

in which X is CN or CONR$^1$R$^2$, where R$^1$ and R$^2$ can be identical different and are H or C$_1$–C$_4$-alkyl, is reacted with a triacyl phosphite of the formula III

P(OCOR$^3$)$_3$ in which the radicals R$^3$, which can be identical or different, are C$_1$–C$_{18}$-alkyl or aryl which is optionally substituted by C$_1$–C$_4$-alkyl, NO$_2$ or OC$_1$–C$_4$-alkyl, and the product obtained is hydrolyzed. The reaction can be carried out with or without solvent. An inert organic solvent is preferably used, in particular a halogenated hydrocarbon, such as 1,2-dichloroethane. The reaction components are expediently employed in essentially stoichiometric amounts. The reaction temperature is in general in the range from −10° C. to 140° C.

An acidic hydrolysis is then carried out, a hydrohalic acid, such as hydrochloric acid, in particular being used. When using hydrochloric acid, an ammonium chloride is then contained in the aqueous mixture used as a starting material for the process according to the invention.

The acid is in general employed in an excess, in particular in an amount of at least 2 equivalents. The temperature at which the hydrolysis is carried out is in general in the range from approximately 10 to 180° C.

The phosphonomethylglycine obtained in the hydrolysis using an excess of acid is dissolved in the aqueous phase. The carboxylic acid $R^3COOH$ formed in the hydrolysis in general precipitates and is separated in a customary manner.

The phosphonomethylglycine can be precipitated by adjusting the aqueous phase to a pH in the range from 0.5 to 2.0 and recovered in a customary manner. The adjustment of the pH is carried out by addition of an alkali metal or alkaline earth metal hydroxide, in particular by addition of NaOH or KOH.

The mixture remaining after the recovery of the phosphonomethylglycine is employed as a starting material for the process according to the invention. If it contains an organic solvent, this is essentially removed from the mixture by distillation. The mixture is an aqueous solution essentially having the following composition (in each case based on the total weight of the mixture):

N-phosphonomethylglycine 0.5 to 3% by weight in particular 0.5 to 2.5% by weight
aminomethylphosphonic acid 0.01 to 0.5% by weight
glycine 0.1 to 0.4% by weight
bis(phosphonomethyl)glycine 0.2 to 0.8% by weight
ammonium halides/alkali metal or alkaline earth metal halides 10 to 25% by weight, in particular 12 to 20% by weight.

The process for the preparation of N-phosphonomethylglycine via the hexahydrotriazine of the formula II is detailed in PCT/EP00/13162. The contents of this application are also included in the present application by way of reference.

In step (a) of the process according to the invention, the aqueous mixture is adjusted to a pH in the range from 2 to 8, in particular 2.5 to 6.5, and particularly preferably to approximately 4 to 5. This adjustment is carried out using a suitable acid or base, such as hydrochloric acid, sulfuric acid, phosphoric acid, sodium hydroxide or potassium hydroxide.

In step (b) of the process according to the invention, the mixture is then subjected to a separation on a selective nanofiltration membrane. Nanofiltration is understood as meaning, like ultrafiltration and reverse osmosis, a pressure-driven membrane separation process using a positive osmotic pressure on one side of the membrane, which is above the osmotic pressure of the solution to be treated (where the osmotic pressure is in particular determined by the retention behavior of the membrane). Nanofiltration membranes are in general applied for mechanical reasons to a mono- or multilayer substructure as support made of the same material as or a different material than the membrane. The separating layers can consist of organic polymers, ceramic, metal or carbon. Frequently, membranes made of crosslinked aromatic polyamides are used. Preferred membranes according to the invention have anionic groups, for example sulfonic acid groups, and therefore exhibit a negative charge. Suitable nanofiltration membranes are known to the person skilled in the art and commercially obtainable. Examples are the Desal-5 membranes of Desalination Systems, Escondido, USA, the NF membranes of the Filmtec Corp., Minneapolis, USA (e.g. NF 70, NF 50, NF 40 and NF 40HF), SU 600 membrane of Toray, Japan, and the NTR membranes of Nitto Electric, Japan (e.g. NTR 7450 and NTR 7250 membranes), cf. WO 96/33005.

Preferred membranes according to the invention have separation limits of from 50 to 1000 D, preferably 100 to 500 D.

In practice, the nanofiltration membranes are incorporated into 'membrane modules' (membrane units). All module geometries which are mechanically stable under the temperature and pressure conditions of the process according to the invention are suitable here. Flat, tubular, multichannel element, capillary or wound geometry, for example, are suitable. Appropriate embodiments are supplied commercially.

The temperature at which step (b) is carried out is not critical. In general, the temperature is chosen such that damage to the membrane is avoided. In the case of polymer membranes, the process is therefore expediently carried out at a temperature of less than 50° C. Ceramic or metal membranes, however, can also be employed at higher temperature.

Step (b) is a pressure-driven separation process. The driving force for the separation is thus a pressure difference over the membrane, which must be greater than the osmotic pressure of the mixture employed. Expediently, the process is carried out at a transmembrane pressure between retentate side and permeate side of 30 to 100 bar.

To avoid concentration polarization on the feed side of the membrane and deposition of crystallized components, the feed solution is generally passed over the membrane in crossflow. The retentate is at least partially recycled here. Preferably, the process is carried out at a flowing-over rate of the feed solution in the range from 0.1 to 5 m/s. The flowing-over rate depends on the module geometry and can be determined in a simple manner by the person skilled in the art.

Step (b) leads to a separation of the mixture employed into a retentate, which is enriched with N-phosphonomethylglycine in comparison to the feed solution, and a permeate, which is enriched with the ammonium halide, alkali metal or alkaline earth metal halide. Surprisingly, it is thus possible to separate N-phosphonomethylglycine and the halides mentioned, although the molecular weight difference of the components to be separated is not very high and the N-phosphonomethylglycine is not quantitatively present in salt form.

Step (b) of the process according to the invention can be realized in different embodiments, depending on the desired degree of recovery of N-phosphonomethylglycine and depending on the desired degree of depletion of the halides. Thus, step (b) can be carried out as a pure concentration stage, in which the retentate enriched in N-phosphonomethylglycine and the permeate enriched in halides are obtained. Here, the depletion of the halides on the retentate side of the membrane is limited by the osmotic pressure.

If a continuing depletion of the halides in the retentate is desired, at least one diafiltration stage follows the concentration stage. For this purpose, just as much water is fed to the retentate of the concentration stage as permeate has been separated. The dilute retentate is then fed to the diafiltration stage, which is carried out under the same conditions and using the same membrane as described above. In this way, a retentate which is depleted in halides is obtained, which, if desired, can be concentrated in a further step, for example by distilling off the water.

In order to obtain a high depletion of halides, step (b) can also be carried out as a pure diafiltration stage. Here, the solution obtained from stage (a) is separated as described above, where, however, just as much water is fed to the retentate as is separated as permeate. A retentate is obtained which is concentrated for the recovery of N-phosphonomethylglycine, for example by removing the water by means of distillation or reverse osmosis.

The pure concentration, the concentration with subsequent diafiltration and the pure diafiltration can all be carried out in one stage or a number of stages. In the multistage procedure, the permeate of the preceding stage is fed to a subsequent stage and the retentate of the subsequent stage is fed into the feed solution of the preceding stage. Here, the individual stages can be equipped with the same membrane or with different membranes. With the multistage procedure, a better retention of N-phosphonomethylglycine or the salts thereof is achieved.

The retentate obtained after step (b) can be used further as such. Depending on concentration and purity, it can be subjected to a concentration or purification or disposed of. In general, however, the retentate is treated further as in step (c) for the recovery of the N-phosphonomethylglycine contained therein.

Step (b) of the process according to the invention is illustrated below with the aid of the figures:

For the continuous separation of the mixture, the feed solution F is fed in a crossflow procedure to a membrane unit M having a housing in which a membrane is situated. The feed solution F flows over the membrane, the retentate R being removed. If desired, some of the retentate R is fed. The permeate P is removed.

The carrying-out of step (b) as a pure diafiltration is is also envisaged. The feed solution F is fed to the membrane unit M after dilution with water and separated as described above.

The feed solution F is fed via line 1 to the first membrane unit M1 in a crossflow procedure. A separation into a retentate R1 and a permeate P1 takes place. The retentate R1 is partially expelled and partially fed back into the feed solution. The permeate P1 is fed back in a crossflow procedure to the second membrane unit M2. A separation into a retentate R2 and a permeate P2 takes place. The retentate R2 is fed to the feed solution F. If desired, some of the retentate R2 is fed back into the feed solution of the membrane unit M2. The perlmeate P2 is fed into the third membrane unit M3 in a cross flow procedure. The retentate R3 obtained in the separation is fed to the feed of the membrane unit M2. If desired, some of the retentate R3 is fed back into the feed solution of the membrane unit M3. The permeate P3 is expelled.

In step (c) of the process according to the invention the recovery of the N-phosphonomethylglycine from the retentate obtained in stage (b) takes place. For this purpose, the pH of the retentate is adjusted to 0.5 to 2.0, in particular 0.8 to 1.5, by addition of an acid, for example hydrochloric acid or sulfuric acid. If desired, the retentate is concentrated, for example by distillation or reverse osmosis. It is also possible to add precipitation aids in order to precipitate the phosphonomethylglycine as completely as possible. The precipitation aid used is preferably a water-miscible solvent, such as methanol, ethanol, isopropanol, acetone etc. The solvents can be recovered from the mother liquor by distillation and reused.

The phosphonomethylglycine is obtained in crystalline form. It can be recovered in a customary manner, for example by filtration.

The permeate obtained in step (b) can be disposed of or fed to further processing. Preferably, it is rendered alkaline, e.g. to pH 13–14, using a strong base, in order to recover the ammonia or the corresponding amine from the ammonium halides contained in the permeate. Suitable bases are alkali metal or alkaline earth metal hydroxides, such as sodium hydroxide, potassium hydroxide or calcium hydroxide. The ammonia released in this way can be recovered, for example by distillation or stripping with an inert gas, such as air or nitrogen.

The process according to the invention or each stage taken per se can be carried out continuously, batchwise or as a semi-batch process.

The advantages of the process according to the invention lie in the concentration of the N-phosphonomethylglycine and thus in an increase in yield in the preparation. Moreover, a separation of the crop protection components from the wastewater is achieved. Finally, a separation of the chlorides contained in the starting mixture takes place, which makes possible a simpler recovery of ammonia from the ammonium halides.

The following examples illustrate the invention without restricting it.

EXAMPLE 1

In a 2 l stirring flask having a Teflon blade stirrer and reflux condenser, 284 g of ammonium benzoate are introduced into 1000 ml of 1,2-dichloroethane and 91.5 g of phosphorus trichloride are added dropwise under a nitrogen atmosphere in the course of 30 min. The temperature rises during the course of this to a maximum of 36° C. The mixture is then stirred at 25 to 36° C. for a further 30 min. The batch is filtered through a pressure suction filter and the filter cake is washed a further two times with 500 g of dichloroethane each time under nitrogen (2054 g of filtrate).

In a 2 l stirring flask having a Teflon blade stirrer and reflux condenser, the filtrate is introduced at room temperature and the hexahydrotriazine IIa (X=CN) (45.54 g) is added. The mixture is heated to 80° C. with stirring in the course of 30 min and stirred at 80° C. for a further 30 min. The solution is allowed to cool and hydrolyzed directly following this.

To this end, the substances employed are metered at 130° C. and 8 bar into a tubular reactor (volume about 600 ml) having a preconnected static mixer (1265 g/h of the dichloroethane solution from the preceding stage, 207 g/h of 20% strength HCl). The residence time is 30 min. A forerun is discarded. For further processing, the two-phase mixture obtained is collected for 60 min. The phases are separated at 60° C. and the water phase is extracted twice with 100 g of dichloroethane each time.

In a round-bottomed flask having a Teflon blade stirrer, the dichloroethane still contained in the water phase is firstly stripped at 60° C. by passing in nitrogen for one hour. The pH is then adjusted to pH=1.0 at 40 to 60° C. in the course of 15 min using 50% strength sodium hydroxide solution. The resulting suspension is stirred at 40° C. for a further 3 h, allowed to cool to room temperature and the precipitated product is filtered off with suction and subsequently washed with 150 g of ice water. The solid obtained is dried at 70° C. and 50 mbar for 16 h.

Yield: 54.6 g of phosphonomethylglycine (purity 96.2% according to HPLC), corresponding to 80% yield, based on $PCl_3$.

The mother liquor from the crystallization has the following composition:

| | |
|---|---|
| 2.10% by weight of | N-phosphonomethylglycine |
| 0.10% by weight of | aminomethylphosphonic acid |
| 0.20% by weight of | glycine |
| 0.45% by weight of | bis(phosphonomethyl)glycine |
| 16.70% by weight of | $NaCl/NH_4Cl$ |

The pH of the mother liquor is subsequently adjusted to 4 using 50% strength NaOH. The mother liquor is then concentrated batchwise in a stirred pressure cell. The stirred pressure cell is equipped with a nanofiltration membrane of the type Desal 5 DK from Desal-Osmotics. The nanofiltration is carried out at 40° C. and 80 bar. The mean specific permeate flow is 5.29 $kg/m^2h$. A retention of N-phosphonomethylglycine of 99.22% and a depletion of chloride salts of 86.26% results. The results are compiled in table 1 below.

TABLE 1

| Amount (g) Concentration | Mother liquor 1550 | Retentate 217 | Permeate 1333 |
|---|---|---|---|
| N-Phosphonomethyl-glycine | 2.10% by weight | 14.60% by weight | 650 ppm |
| Aminomethyl-phosphonic acid | 0.10% by weight | 0.70% by weight | 23 ppm |
| Glycine | 0.20% by weight | 0.30% by weight | 0.18% by weight |
| Bis(phosphono-methyl)glycine | 0.45% by weight | 3.20% by weight | 23 ppm |
| $NaCl/NH_4Cl$ | 16.70% by weight | 16.40% by weight | 16.75% by weight |

For the recovery of the N-phosphonomethylglycine, 50.0 g of the retentate and 30.0 g of water were added to a 250 ml round-bottomed flask having a Teflon blade stirrer. 14.24 g of 20% strength HCl were added dropwise to this at 40° C. in the course of 10 minutes until a pH of 1.3 was achieved. The resulting suspension was stirred at 40° C. for a further 3 hours and then allowed to cool to room temperature. The precipitated phosphonomethylglycine was filtered off with suction and washed with 20 g of water. The solid was dried at 70° C. and 50 mbar for 16 hours.

Yield: 4.10 g of solid (contains 94.7% of phosphonomethylglycine corresponding to a recovery rate of 53%)

Analysis: NaCl: 0.0% Phosphonomethylglycine 94.7% (HPLC)

Mother liquor: 106.8 g of solution

EXAMPLE 2

Batchwise Two-Stage Concentration of the Mother Liquor Obtained as in Example 1

The pH of the mother liquor was adjusted to 4 as described in example 1. The mother liquor was concentrated batchwise in a stirred pressure cell of the type described in example 1 having the same membrane. The conditions were as described in example 1. The permeate was fed to a further stirred pressure cell of the same type having the same membrane and concentrated. The concentration was carried out at 40° C. and 40 bar. The mean specific permeate flow in the second stage is 25.70 $kg/m^2h$. The retention of N-phosphonomethylglycine calculated over both nanofiltration stages is 99.99% and the depletion of chloride salts is 77.82%. The results are compiled in table 2 below.

TABLE 2

| Amount (g) Concentration | Mother liquor 1550 | Retentate Stage 1 217 | Retentate Stage 2 133.3 | Permeate 1199.7 |
|---|---|---|---|---|
| N-Phosphono-methylglycine | 2.10% by weight | 14.60% by weight | 6320 ppm | 20 ppm |
| Aminomethyl-phosphonic acid | 0.10% by weight | 0.70% by weight | 230 ppm | — |
| Glycine | 0.20% by weight | 0.30% by weight | 9630 ppm | 930 ppm |
| Bis(phosphono-methyl)glycine | 0.45% by weight | 3.20% by weight | 230 ppm | — |
| $NaCl/NH_4Cl$ | 16.70% by weight | 16.40% by weight | 16.40% by weight | 16.79% by weight |

We claim:

1. A process for the recovery of N-phosphonomethylglycine from an aqueous mixture which contains N-phosphonomethylglycine, ammonium halides, and alkali metal or alkaline earth metal halides and optionally organic impurities in dissolved form, where
    (a) the pH of the mixture is adjusted to a value in the range from 2 to 8,
    (b) a separation of the mixture on a selective nanofiltration membrane is performed, a retentate which is richer in N-phosphonomethylglycine and poorer in halides and a permeate which is richer in halides and poorer in N-phosphonomethylglycine being obtained, and
    (c) the N-phosphonomethylglycine is recovered from the retentate.

2. A process as claimed in claim 1, the mixture originating from the preparation of N-phosphonomethylglycine, in which a triazine of the formula II

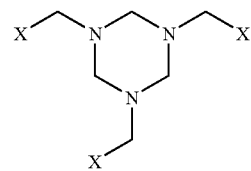

in which X is CN or $CONR^1R^2$, where $R^1$ and $R^2$ can be identical or different and are H or $C_1$–$C_4$-alkyl, is reacted with a triacyl phosphite of the formula III

$P(OCOR^3)_3$ in which the radicals $R^3$ are $C_1$–$C_{18}$-alkyl or aryl which is optionally substituted by $C_1$–$C_4$-alkyl, $NO_2$ or $OC_1$–$C_4$-alkyl,
    and the product obtained is hydrolyzed using a hydrohalic acid.

3. A process as claimed in claim 2, a mixture being used which was obtained as a mother liquor after reaction of the triazine of the formula II with the triacyl phosphite of the formula III, hydrolysis of the, product obtained using hydrochloric acid and separation of the N-phosphonomethylglycine at pH 0.5 to 2.

4. A process as claimed in claim 3, the mixture containing 0.5 to 3% by weight of N-phosphonomethylglycine and 10 to 25% by weight of chloride salts.

5. A process as claimed in claim 1, the pH of the mixture being adjusted to a value in the range from 2.5 to 6.5.

6. A process as claimed in claim 1, a membrane having a separation limit in the range from 50 to 1000 D being used in step (b).

7. A process as claimed in claim 6, a membrane having a separation limit in the range from 100 to 500 D being used.

8. A process as claimed in claim 1, the separation of the mixture in step (b) being carried out at a transmembrane pressure between retentate side and permeate side in the range from 30 to 100 bar.

9. A process as claimed in claim 1, the separation of the mixture in step (b) being carried out at a flowing-over rate in the range from 0.1 to 5 m/s.

10. A process as claimed in claim 1, the separation in step (b) being carried out in a number of stages by feeding the permeate from one stage to the subsequent stage as a feed solution.

11. A process as claimed in claim 10, the retentate of the second or a further stage being at least partially fed to the first or the preceding stage.

12. A process as claimed in claim 1, the retentate obtained in stage (bl being subjected to at least one diafiltration step.

13. A process as claimed in claim 1, the permeate being treated with a strong base in order to release the ammonia or amine contained in the ammonium halides.

* * * * *